United States Patent [19]

Boelle et al.

[11] 4,196,201

[45] Apr. 1, 1980

[54] NON-IRRITATING EYE MAKE-UP REMOVER COMPOSITION

[75] Inventors: Jean-Paul Boelle; Constantin Koulbanis; Arlette Zabotto, all of Paris, France

[73] Assignee: L'Oreal, Paris, France

[21] Appl. No.: 905,455

[22] Filed: May 12, 1978

[30] Foreign Application Priority Data

May 18, 1977 [FR] France .................................. 77 15292

[51] Int. Cl.$^2$ ............................................. A61K 31/70
[52] U.S. Cl. ........................................ 424/180; 536/1; 536/4; 424/361; 424/362; 424/329
[58] Field of Search ............... 424/180, 361, 362, 329; 536/120, 4, 1

[56] References Cited

U.S. PATENT DOCUMENTS

| | | | |
|---|---|---|---|
| 3,190,927 | 6/1965 | Patton et al. | 536/120 |
| 3,449,318 | 6/1969 | Roth et al. | 536/120 |
| 3,547,828 | 12/1970 | Mansfield et al. | 536/4 |
| 4,011,389 | 3/1977 | Langdon | 536/120 |

*Primary Examiner*—Johnnie R. Brown
*Assistant Examiner*—Blondel Hazel
*Attorney, Agent, or Firm*—Cushman, Darby & Cushman

[57] ABSTRACT

New surface active agents for use in eye make-up remover compositions, which are not irritating and do not provoke stinging on contact with the ocular mucous, are disclosed.

10 Claims, No Drawings

NON-IRRITATING EYE MAKE-UP REMOVER COMPOSITION

An object of the present invention is to provide an eye make-up remover composition which is not irritating and does not provide ocular difficulties for the user.

Numerous eye make-up remover compositions which permit the removal of eye make-up have been proposed. Although those prior eye make-up remover compositions are not irritants to the ocular mucous, nevertheless they have been established to exhibit certain disadvantages on use, and notably the disadvantage of provoking a stinging sensation or some ocular difficulty for the user.

Generally, during the removal of eye make-up, it is frequently only inadvertence which causes the make-up remover to contact the ocular mucous and then to provoke certain irritation or stinging sensations, which at times can lead to certain complications.

The development of eye make-up remover compositions, which do not provide irritation or ocular difficulty on use presents numerous difficulties, because such compositions contain many diverse indispensible ingredients which in certain cases can react with each other or can, in the long run, suffer degradation following microbial contamination.

Extensive research has been undertaken to provide an eye make-up remover composition which is both non-irritating, which does not cause stinging or smarting and which exhibits excellent long-lasting and stability characteristics.

The present invention is directed to a new industrial product which is an eye make-up remover composition which is non-irritating to the ocular mucous and which, on contact, does not provoke ocular difficulty, which composition is contained in an aqueous solution and comprises:

(a) at least one surface active agent selected from the group consisting of alkyl polyglycosides and hydroxyalkyl polyglycosides, wherein the alkyl contains 11 to 18 carbon atoms and wherein the polyglycoside contains from 5 to 25 repeating glucose units;

(b) at least one preservative agent selected from the group consisting of sodium ethyl mercurithiosilicylate, a chlorhexidine salt such as the digluconate, the diacetate or the dihydrochloride salts; a salt of phenyl mercury such as the nitrate of phenyl mercury; a mixture of 30 weight percent sodium benzoate and 70 weight percent monochloracetamide; at least one quaternary compound having the formula

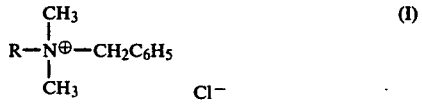

wherein R is an alkyl of 12 to 18 carbon atoms or a mixture of such alkyls such as, for example $C_{12}$–$C_{14}$ and $C_{14}$–$C_{16}$ mixtures; and mixtures of said preservative agents; and (c) a phosphate buffer, the pH of said composition being from 6.5 to 7.5.

The eye make-up remover composition of the invention is preferably in the form of a lotion. The base liquid forming said lotion is either sterilized, demineralized water or flower water extract (such as rose water, cornflower water, camomile water and the like) or mixtures thereof.

The surface active agents of the composition of the invention are, as mentioned above, either alkyl polyglycosides or hydroxyalkyl polyglycosides.

The alkyl polyglycosides are known compositions and are described in French brevet No. 2 017 240, which is incorporated by reference herein.

It is believed that the hydroxyalkyl polyglycosides are novel compounds and compositions. The method of preparing the hydroxyalkyl polyglycosides is the same as that used for the preparation of alkyl polyglycosides.

The number of repeating glucose units in the polyglycoside chain is from 5 to 25.

The alkyl radical of the alkyl polyglycoside preferably derives from alcohols, such as dodecanol, tetradecanol, hexadecanol, or mixtures thereof.

The hydroxyalkyl radical of the hydroxyalkyl polyglycosides is derived preferably from diols, such as dodecanediol-1,2; tetradecanediol-1,2; hexadecanediol-1,2 or mixtures thereof, some of which are known commercially as ADOL 11/14 and ADOL 15/18 and sold by Ashland.

In a preferred embodiment, the surface active agent is present in the compositions at a concentration of from about 0.5 to 5%; the exact concentration depends on the degree of viscosity that is desired in the ultimate product.

The preservative agent of the lotions is generally present in amounts ranging from 0.002% to 0.3%, preferably from 0.02 to 0.2%.

Among the compounds of formula I above which can be used, are those including myristyl-cetyl dimethyl benzylammonium chloride and lauryl-myristyl benzylammonium chloride.

According to one embodiment of the invention, compounds of formula I are used in combination with ethylene diamine tetraacetic acid.

The phosphate buffer in the compositions acts to maintain the pH between 6.5 and 7.5, preferably between 7 and 7.2.

It has been established that the dipotassium hydrogen phosphate/potassium dihydrogen phosphate buffer does not provoke irritation or stinging and moreover does not inhibit the effect of the preservative agent.

The make-up remover lotion of the invention can equally contain other conventional adjuvants, such as, for example, humectant agents, emollients, perfumes and colorants.

Of course the adjuvants should not be capable of provoking irritation or stinging of the ocular mucous.

Among the humectant agents contemplated are hexylene glycol, polyethylene glycol 600, etc.

Among the emollients which are contemplated are Allantion, azulene, etc.

One aspect of the invention is in the new industrial products; the hydroxyalkyl polyglycosides in which the alkyl moiety has 11 to 18 carbon atoms and in which the polyglycoside chain contains 5 to 25 repeating glucose units.

According to the invention the hydroxyalkyl radicals, of the hydroxyalkyl polyglycosides, are derived from α-diols selected from the group consisting of dodecanediol-1,2; tetradecanediol-1,2; hexadecanediol-1,2 and mixtures thereof.

These hydroxyalkyl polyglycosides have superior solubility characteristics, as measured in 5% solution of the hydroxyalkyl glycoside in 25% NaCl - water solution at 100° C.

Another aspect of the invention is the process of making the new hydroxyalkyl polyglycosides. The process comprises reacting D-glucose in the presence of n-butanol and sulfuric acid, removing the n-butanol from the reaction mass, and then heating the reaction mass with an α-diol selected from the group consisting of dodecanediol-1,2; tetradecanediol-1,2; hexadecanediol-1,2 and mixtures thereof.

The reaction temperature of the step of reacting the α-diol with the reaction mass may range from 125° to 128° C.

The following non-limiting examples are illustrative of the present invention, as to the preparation of certain surface active agents and in particular of the hydroxyalkyl polyglycosides of the invention and of various make-up remover compositions of the invention. All parts and percentages are by weight unless otherwise specified.

EXAMPLE I

A hydroxyalkyl polyglycoside, in which the alkyl contains 12 carbon atoms is obtained by following the procedure below:

5 ml of sulfuric acid (10% by volume) is added to 2.4 liters of n-butanol. The resulting mixture is heated to reflux (118° C.), and then 900 g (5 moles) of D-glucose is added in fractions, over a period of one hour, while slowly distilling off the butanol.

After four and one-half hours, dissolution of the glucose is completed; and the reaction mass has a vascous yellow liquid appearance.

The the reaction mass, thus obtained, is added 202 g (1 mole) of dodecanediol-1,2; and the mixture is progressively heated to a temperature of 125°–128° C. for thirty minutes. The last traces of butanol are removed under reduced pressure, 25 to 30 mm (mercury). After about 30 minutes, the reaction mixture cools to a temperature of about 60° C. Then the reaction mixture is dissolved in 300 ml of isopropanol and 200 ml of 0.1N sodium hydroxide. The mixture of solvents is removed from the product by distillation at reduced pressures, and after cooling the reaction mass is filtered (ground) and washed twice with a liter of acetone. The resulting solution, 10% product, is only slightly turbid; the turbidity can easily be eliminated by filtration.

After drying, e.g. by atomization, a water-soluble clear beige product is obtained. The turbidity point of a 0.5% solution of the product in a 25% sodium chloride water solution is higher than 100° C.

EXAMPLE II

According to the procedures of Example I, a hydroxyalkyl polyglycoside in which the alkyl contains 12 carbon atoms, is prepared employing the following reagents:

| n-butanol | 240 ml |
| --- | --- |
| Sulfuric acid | |
| (10% by volume) | 0.5 ml |
| D-glucose | 90 g (0.5 mole) |
| Dodecanediol-1,2 | 33.8 g (0.16 mole) |
| Isopropanol | 30 ml |
| Sodium hydroxide (0.1N) | 20 ml |
| Acetone | 200 ml |

The turbiidty point of the product (0.5% in 25% sodium chloride water solution) is hihger than 100° C.

EXAMPLE III

According to the procedures described in Example I, a hydroxyalkyl polyglycoside in which the alkyl contains 12 carbon atoms, was produced by reacting the following reagents:

| n-butanol | 240 ml |
| --- | --- |
| Sulfuric acid | |
| (10% by volume) | 0.5 ml |
| D-glucose | 90 g (0.5 mole) |
| Dodecanediol-1,2 | 14.45 g (0.0715 mole) |
| Isopropanol | 30 ml |
| Sodium hydroxide (0.1N) | 20 ml |
| Acetone | 200 ml |

The turbidity point of the product as a 0.5% solution in a 25% sodium chloride water solution is higher than 100° C.

EXAMPLE IV

By a method described in Example I, an alkyl polyglycoside in which the alkyl contains 12 carbon atoms was produced by reacting the following reagents:

| n-butanol | 240 ml |
| --- | --- |
| p-toluene sulfonic acid | |
| (10%) | 0.5 ml |
| D-glucose | 90 g (0.5 mole) |
| Dodecanol | 18.6 g (0.1 mole) |
| Isopropanol | 30 ml |
| Sodium hydroxide (0.1N) | 20 ml |
| Acetone | 200 ml |

The turbidity point of the product measured at a 0.5% concentration in 25% sodium chloride water solution was higher than 100° C.

EXAMPLE V

Following the method described in Example I, mixed hydroxyalkyl polyglycosides in which the alkyls contained 14 to 16 carbon atoms were produced by reacting the following reagents:

| n-butanol | 240 ml |
| --- | --- |
| Sulfuric acid | |
| (10% by volume) | 0.5 ml |
| D-glucose | 90 g (0.5 mole) |
| Mixture of diols of alkanes containing 14 to 16 carbon atoms | 25.5 g (0.1 mole) |
| Isopropanol | 30 ml |
| Sodium hydroxide (0.1N) | 20 ml |
| Acetone | 200 ml |

The product which was obtained, in the form of a clear beige powder, was soluble in water.

The turbidity point at 0.5% in water was higher than 100° C.

EXAMPLES OF COMPOSITIONS

EXAMPLE A

According to the invention, an eye make-up remover composition is prepared by admixing the following ingredients:

| | |
|---|---|
| Composition of Example IV | 1.8 g |
| Hexyleneglycol | 1 g |
| Potassium dihydrogen phosphate | 0.102 g |
| Dipotassium hydrogen phosphate, 3H$_2$O | 0.394 g |
| Chlorhexidine digluconate | 0.75 g |
| Demineralized sterile water, q.s.p. | 100 g |

EXAMPLE B

An eye make-up remover composition according to the invention which upon contact with the ocular mucous provokes no irritation or ocular difficulty is prepared by admixing the following ingredients:

| | |
|---|---|
| Allantoin | 0.05 g |
| Compound of Example I | 1 g |
| Polyethylene glycol 600 | 3 g |
| Potassium dihydrogen phosphate | 0.204 g |
| Dipotassium hydrogen phosphate, 3H$_2$O | 0.788 g |
| Sodium ethylmercurithio-salicylate | 0.003 g |
| Sterilized, demineralized water, q.s.p. | 100 g |

EXAMPLE C

An eye make-up remover lotion according to the invention is prepared by admixing the following ingredients:

| | |
|---|---|
| Compound of Example IV | 1.8 g |
| Potassium dihydrogen phosphate | 0.102 g |
| Dipotassium hydrogen phosphate, 3H$_2$O | 0.394 g |
| Hexylene glycol | 1.00 g |
| Lauryl, myristyl, dimethyl-benzyl ammonium chloride | 0.0288 g |
| Ethylene diamine tetraacetic acid | 0.0104 g |
| Sterilized, demineralized, water, q.s.p. | 100 g |

EXAMPLE D

An eye make-up remover lotion, according to the invention, is prepared by admixing the following ingredients:

| | |
|---|---|
| Allantoin | 0.05 g |
| Hexylene glycol | 1.00 g |
| Compound of Example I | 1.50 g |
| Potassium dihydrogen phosphate | 0.102 g |
| Dipotassium hydrogen phosphate, 3H$_2$O | 0.394 g |
| Chlorhexidine dichloride | 0.080 g |
| Sodium benzoate | 0.03 g |
| Monochloroacetamide | 0.07 g |
| Sterilized, demineralized water, q.s.p. | 100 g |

EXAMPLE E

An eye make-up remover lotion, according to the invention, is prepared by admixing the following ingredients:

| | |
|---|---|
| Compound of Example IV | 1.8 g |
| Potassium dihydrogen phosphate | 0.102 g |
| Dipotassium hydrogen phosphate, 3H$_2$O | 0.394 g |
| Hexylene glycol | 1.00 g |
| Myristyl, cetyl, dimethyl benzylammonium chloride | 0.025 g |
| Sterilized, demineralized water, q.s.p. | 100 g |

What is claimed is:

1. An eye make-up remover composition which is non-irritating and does not provoke ocular difficulties comprising in an aqueous solution:
   (i) 0.5 to 5% by weight of a surface active agent selected from the group consisting of alkyl polyglycosides and hydroxyalkyl polyglycosides, wherein the alkyl of each of said alkyl and hydroxyalkyl polyglycosides has 11 to 18 carbon atoms and wherein said polyglycoside contain 5 to 25 repeating glucose units;
   (ii) 0.002 to 0.3% by weight of a preservative agent selected from the group consisting of sodium ethyl mercurithio-salicylate; a chlorhexidine salt; a phenyl mercury salt; a mixture of 30% by weight sodium benzoate and 70% by weight of monochloracetamide a compound of the formula

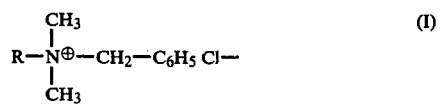

wherein
R is an alkyl of 12 to 18 carbon atoms or mixtures of compounds of formula I; and mixtures of the aforementioned preservative agents; and
   (iii) a phosphate buffer;
the pH of said composition being from 6.5 to 7.5.

2. The composition of claim 1, wherein said preservative agent comprises a mixture of different compounds of formula I, in which R is a mixture and is alkyl of 12 to 14 carbon atoms and alkyl of 14 to 16 carbon atoms.

3. The composition of claim 1, wherein the chlorhexidine salt is chlorhexidine digluconate, chlorhexidine diacetate or chlorhexidine dihydrochloride.

4. The composition of claim 1, wherein the phenyl mercury salt is phenyl mercury nitrate.

5. The composition of claim 1, wherein the preservative agent is a mixture of myristyl-cetyl dimethyl benzylammonium chloride and lauryl-myristyl dimethyl benzylammonium chloride.

6. The composition of claim 5, wherein said preservative agent is admixed with ethylene diamine tetraacetic acid.

7. The composition of claim 1, wherein the amount of preservative agent ranges from 0.02 to 0.2% by weight.

8. The composition of claim 1, wherein the phosphate buffer is dipotassium hydrogen phosphate/potassium dihydrogen phosphate buffer.

9. The composition of claim 1, wherein the pH is from 7 to 7.2.

10. The composition of claim 1, which includes conventional adjuvants including humectants, emollients, perfumes, colorants or mixtures thereof.